United States Patent
Wehrheim et al.

(10) Patent No.: US 10,368,950 B2
(45) Date of Patent: Aug. 6, 2019

(54) DRIVE ARRANGEMENT FOR AN ENDOSCOPIC SHAFT-TYPE INSTRUMENT

(71) Applicant: RICHARD WOLF GMBH, Knittlingen (DE)

(72) Inventors: Frank Wehrheim, Bretten (DE); Alexander Schweigert, Eisingen (DE); Stephan Prestel, Rheinstetten (DE); Sören Münnig, Walzbachtal (DE); Matthias Lambertz, Bretten (DE); Eberhard Körner, Knittlingen (DE)

(73) Assignee: RICHARD WOLF GMBH, Knittlingen (DE)

( * ) Notice: Subject to any disclaimer, the term of this patent is extended or adjusted under 35 U.S.C. 154(b) by 538 days.

(21) Appl. No.: 15/101,498

(22) PCT Filed: Nov. 10, 2014

(86) PCT No.: PCT/DE2014/200625
§ 371 (c)(1),
(2) Date: Jun. 3, 2016

(87) PCT Pub. No.: WO2015/081947
PCT Pub. Date: Jun. 11, 2015

(65) Prior Publication Data
US 2016/0302874 A1    Oct. 20, 2016

(30) Foreign Application Priority Data
Dec. 6, 2013    (DE) .......... 10 2013 225 117

(51) Int. Cl.
*F16H 19/06*    (2006.01)
*A61B 34/30*    (2016.01)
(Continued)

(52) U.S. Cl.
CPC .............. *A61B 34/30* (2016.02); *A61B 34/70* (2016.02); *A61B 34/71* (2016.02); *F16D 3/26* (2013.01);
(Continued)

(58) Field of Classification Search
CPC ......... A61B 34/30; A61B 34/70; A61B 34/71; F16H 19/06
See application file for complete search history.

(56) References Cited

U.S. PATENT DOCUMENTS 3,362,651 A * 1/1968 Sahm ................... B65H 54/103
242/484.6
4,179,944 A * 12/1979 Conner .................. B64C 13/42
192/141
(Continued)

FOREIGN PATENT DOCUMENTS

| EP | 0 054 763 A1 | 6/1982 |
| WO | 2007/146987 A2 | 12/2007 |
| WO | 2013/159932 A1 | 10/2013 |

*Primary Examiner* — David M Fenstermacher
(74) *Attorney, Agent, or Firm* — McGlew and Tuttle, P.C.

(57) ABSTRACT

A drive arrangement for an endoscopic shaft instrument, preferably an instrument which is intended for use in connection with a surgical robot, has a drive arrangement that has an instrument housing (12) on a proximal shaft end. At least one housing shaft (22) is mounted in the instrument housing (12). The shaft is drivingly connected to a traction device which is provided for controlling an instrument head on a distal shaft end. Furthermore, the drive arrangement has a drive unit having at least one drive shaft. The housing shaft (22) can be drivingly connected to said drive shaft. The at least one housing shaft (22) is oriented at an angle to the drive shaft (30) and the drive shaft can be drivingly connected thereto.

19 Claims, 18 Drawing Sheets

(51) Int. Cl.
  *A61B 34/00* (2016.01)
  *F16D 3/26* (2006.01)
(52) U.S. Cl.
  CPC ........ *F16H 19/06* (2013.01); *A61B 2034/301* (2016.02); *A61B 2034/305* (2016.02)

(56) References Cited

U.S. PATENT DOCUMENTS

| | | | | |
|---|---|---|---|---|
| 4,745,815 A * | 5/1988 | Klopfenstein | .......... | B64C 13/38 244/228 |
| 5,035,446 A * | 7/1991 | Arvidsson | .............. | B62D 1/181 280/775 |
| 5,086,900 A * | 2/1992 | Kikuta | .................... | E05B 81/25 192/141 |
| 5,178,411 A * | 1/1993 | Fevre | ...................... | B62D 1/181 280/775 |
| 5,620,078 A * | 4/1997 | Nakamura | .......... | F16H 25/2015 192/142 R |
| 5,910,692 A * | 6/1999 | Saeda | ................... | F16H 25/20 310/13 |
| 6,390,505 B1 * | 5/2002 | Wilson | ................... | B62D 1/181 280/775 |
| 7,025,380 B2 * | 4/2006 | Arihara | ................. | B62D 1/181 280/775 |
| 7,159,904 B2 * | 1/2007 | Schafer | ................. | B62D 1/181 280/775 |
| 8,056,437 B2 * | 11/2011 | Rouleau | ................ | B62D 1/187 74/493 |
| 8,151,668 B2 * | 4/2012 | Oshita | .................... | B62D 1/181 280/774 |
| 8,448,986 B2 * | 5/2013 | Fevre | .................... | B62D 1/181 280/775 |
| 8,979,126 B2 * | 3/2015 | Morinaga | .............. | B62D 1/181 280/775 |
| 9,260,130 B2 * | 2/2016 | Mizuno | ................... | B62D 1/187 |
| 9,610,968 B2 * | 4/2017 | Born | ...................... | B62D 1/181 |
| 9,676,298 B2 * | 6/2017 | Beneker | ............... | B60N 2/0232 |
| 2004/0032121 A1 * | 2/2004 | Schafer | ................. | B62D 1/181 280/775 |
| 2009/0163929 A1 * | 6/2009 | Yeung | ..................... | B25J 9/047 606/130 |
| 2009/0234371 A1 | 9/2009 | Tierney et al. | | |

* cited by examiner

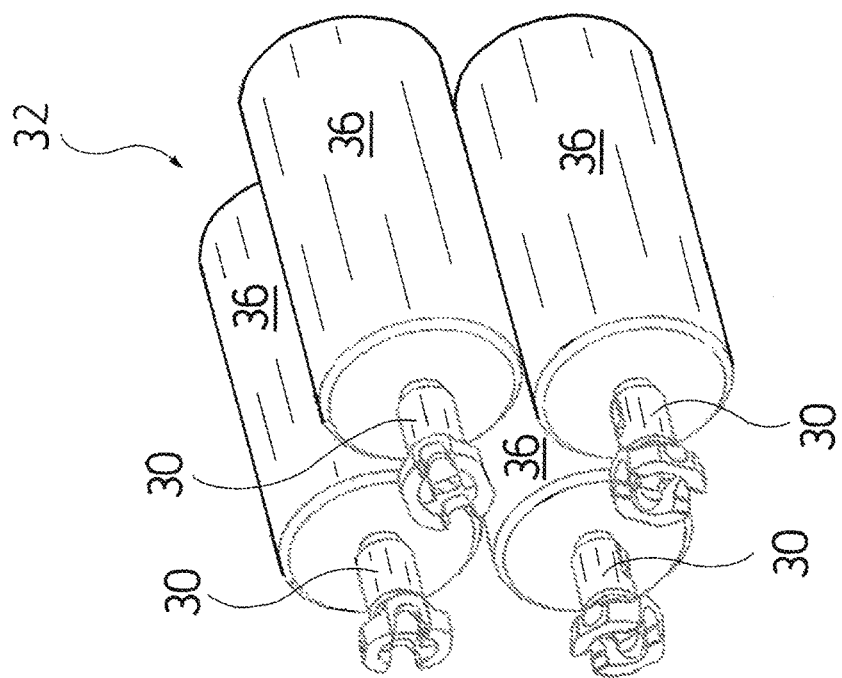
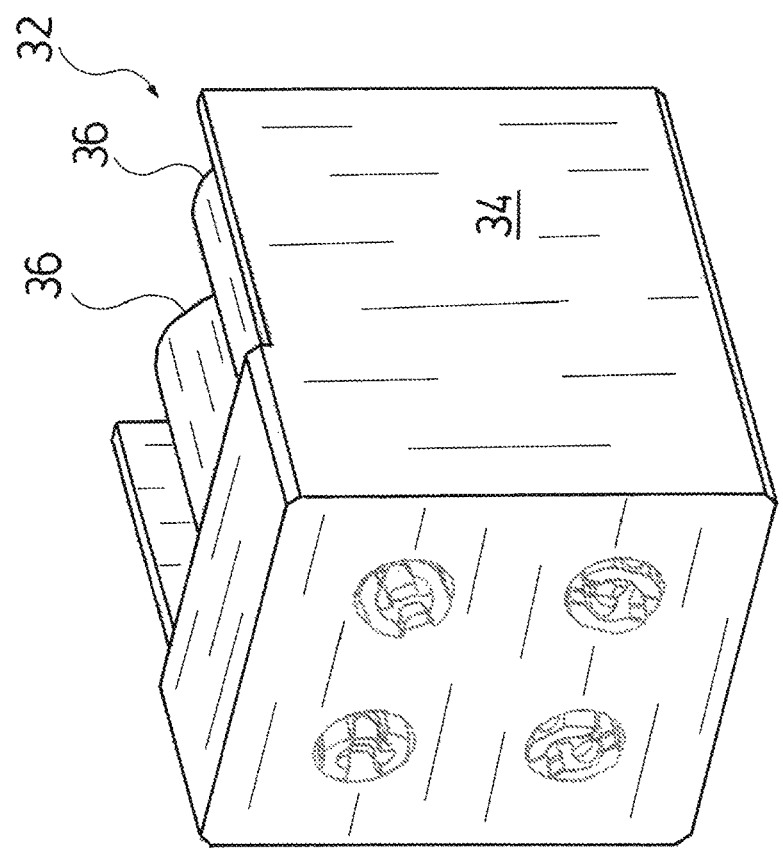
Fig. 6

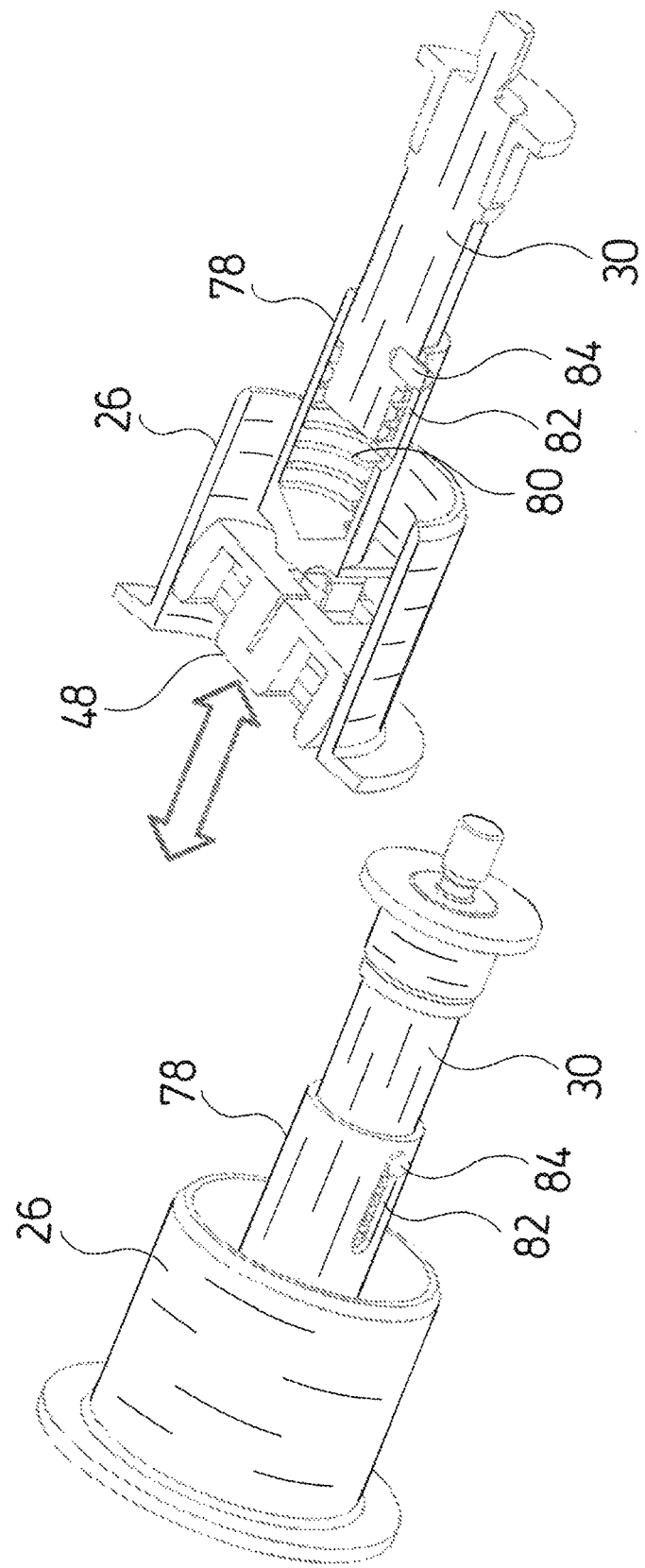

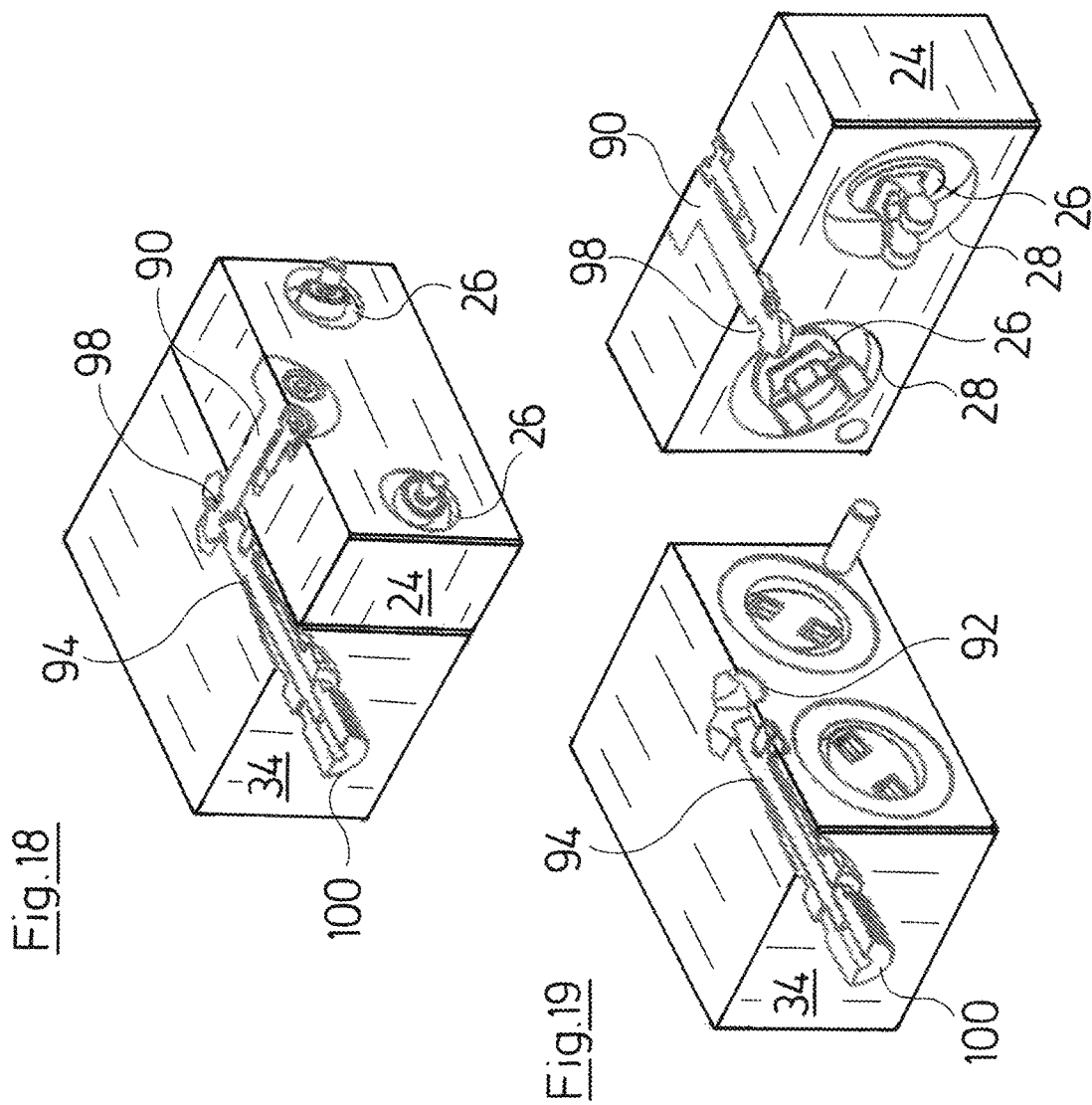

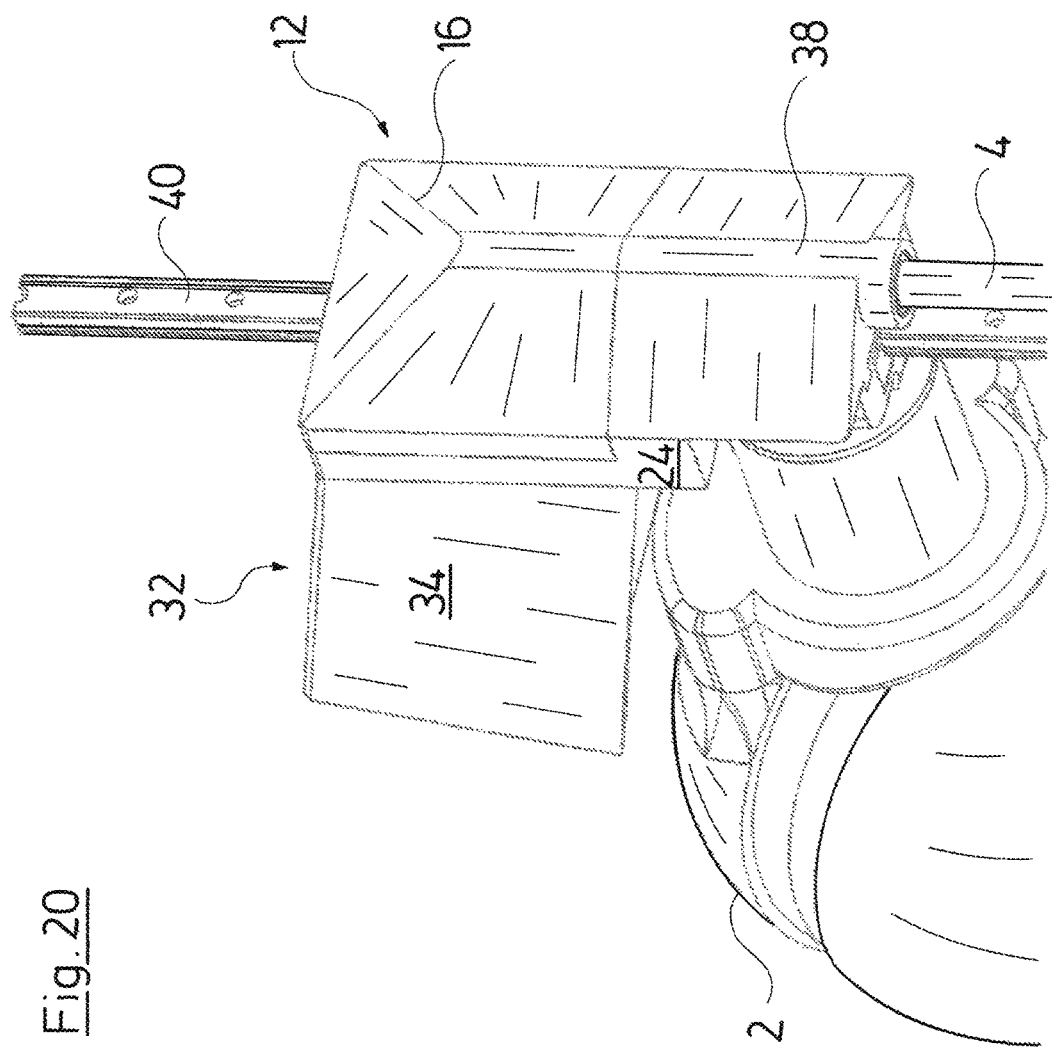

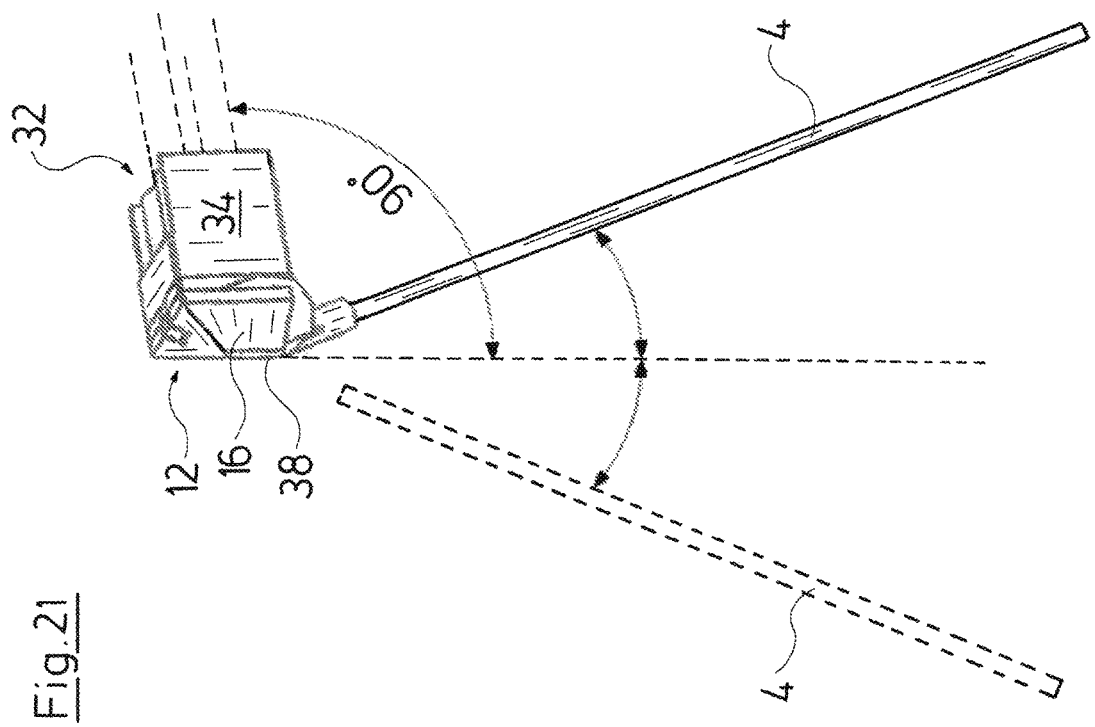

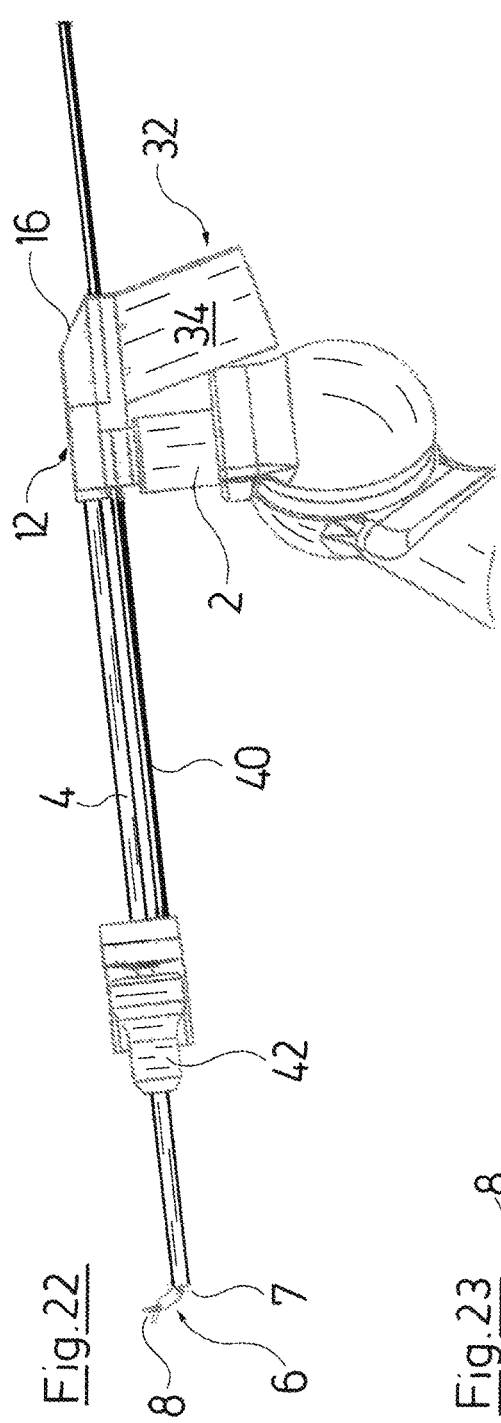
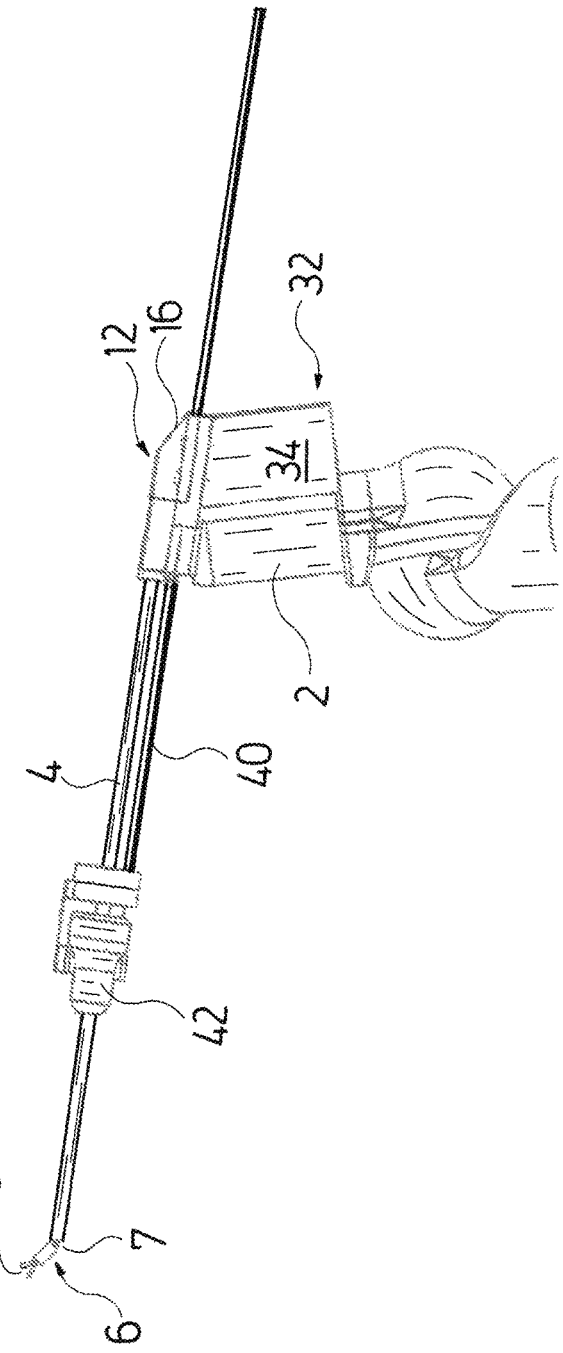
Fig.22
Fig.23

DRIVE ARRANGEMENT FOR AN ENDOSCOPIC SHAFT-TYPE INSTRUMENT

CROSS REFERENCE TO RELATED APPLICATIONS

This application is a United States National Phase Application of International Application PCT/DE2014/200625 filed Nov. 10, 2014 and claims the benefit of priority under 35 U.S.C. § 119 of German Application 10 2013 225 117.3 filed Dec. 6, 2013, the entire contents of which are incorporated herein by reference.

FIELD OF THE INVENTION

The invention relates to a drive arrangement for an endoscopic shank instrument with an instrument housing at the proximal shank end, with at least one housing shaft which is rotatably mounted in the instrument housing and which is repeatedly releasably drive-connected to a pull device, which pull device is provided at a distal shank end for control of an instrument head, and with a drive unit with at least one drive shaft, to which drive shaft the housing shaft is drive-connectable.

BACKGROUND OF THE INVENTION

Operation robots have been applied for some time now in the field of minimal-invasive surgery. These operational robots are provided with at least one, but as a rule with several robot arms, at whose distal ends an endoscopic shank instrument controlled by an operator at a console is arranged in each case. Hereinafter, medical instruments which are used for observing, manipulating or a combination of such functions, for application on or in the body of a living being are to be understood as endoscopic shank instruments. Such an operation robot is known for example from US 2009/0234371 A1.

The shank instruments which are used with this operation robot, at their respective distal shank end comprise an instrument head with a tool which is arranged on this instrument head. Instrument heads which can be angled which is to say angularly bent relative to the shank, are applied in combination with the shank instruments, wherein the tool or a tool carrier which is provided on the instrument head and has a tool, can also be angled with respect to the instrument head. Pull cables which are led through the shank into an instrument housing arranged at the proximal shank end are used for the control of the angling of the instrument head and for the control of the tool or for actuating the instrument head and tool. There, the pull cables are fastened on actuation rollers which are controllably rotatable by way of an actuation motor in each case. The actuation rollers are arranged next to one another in the instrument housing, in a common plane normal to their rotation axis.

The number of the actuation rollers arranged in the instrument housing is determined by the number of degrees of freedom of movement of the instrument head has a significant impact on the size of the instrument housing. The instrument housing is therefore already relatively large with a shank instrument, in whose instrument housing only four actuation rollers are arranged. This size of the instrument housing has been found to be disadvantageous if several of these shank instruments have to be commonly applied in a restricted space, as is the case for example with single port operations, with which the shank instruments are simultaneously led to the field of operation via a common body opening. A large instrument housing has moreover been found to be a hindrance if it is necessary to introduce the shank of these instruments into the body of patient at an as shallow as possible angle to the body surface of this patient.

SUMMARY OF THE INVENTION

Against this background, it is an object of the invention to provide a drive arrangement for an endoscopic shank instrument of the type mentioned above, which permits an instrument housing which is improved with regard to the shaping and/or size and which enlarges the application spectrum of the shank instrument.

The drive arrangement according to the invention, for an endoscopic shank instrument, with which it is preferably the case of a medical instrument which is provided for application in combination with a medical operation robot, comprises an instrument housing at the proximal shank end. At least one, preferably four housing shaft(s) are mounted in the instrument housing. More than four housing shafts can also be arranged, inasmuch as the number of degrees of freedom of movement for the distal instrument head and which are to be controlled demands this. These housing shafts are drive-connected to pull means which are provided for the control of the instrument head at the distal shank end. Pull cables which are led through the instrument shank or become effective directly in the instrument housing preferably serve as pull means. With regard to the housing shafts, it is preferably the case of shafts which carry the actuation rollers for the pull means, said actuation rollers being known per se and being arranged in the instrument housing. The drive arrangement according to the invention moreover comprises a drive unit with at least one, preferably four drive shafts which are aligned parallel to one another. More than four drive shafts can also be arranged, inasmuch as the number of the movement degrees of freedom for the distal instrument head demands this. One of the housing shafts can be drive-connected to each of these drive shafts in each case.

The basic idea of the invention lies in aligning the housing shafts obliquely to the drive shafts which are drive connected to them. Hereby, the direction, in which the housing shafts are obliquely aligned to the drive shafts, is basically arbitrary. One preferably envisages setting all housing shafts in an oblique manner. This oblique setting or positioning of the housing shafts permits a large design freedom with regard to the shaping of the instrument housing and, given a suitable alignment of the housing shafts, permits the creation of instrument housings which are comparatively small. A complete unit of the instrument housing and drive unit, in the case of a suitable oblique positioning of the housing shafts, can moreover be designed such that the shank instrument can be applied with those operations, with which the shank of these instruments must be introduced into the body of a patient at an as shallow as possible angle to the surface of the body of this patient.

With a preferred design with four housing shafts, these are advantageously arranged in a paired manner one after the other in the direction of the longitudinal axis of the instrument shank, on two sides of the instrument shank which are away from one another. Hereby, the housing shafts are preferably arranged in a manner such that the ends of the housing shafts, at which these shafts are drive-connectable to the drive shafts, form the corner points of a rectangle, wherein the shank of the shank instrument is arranged in a plane parallel to the rectangle.

A shaping of the instrument housing, with which this tapers into a tip, in a plane normal to the longitudinal extension of the instrument shank is particularly advantageous. Hereby, the instrument shank is usefully arranged in the direct vicinity of the tip which is formed on the instrument housing. This design permits several shank instruments to be used simultaneously in a restricted space, for example with a single port operation. Thus, for example, already three shank instruments can be applied in the direct proximity to one another, if the instrument housing tapers (in a pointed manner) at an angle of 120°. Typically, the possibility of applying even more shank instruments next to one another in a restricted space is given due to the reduction of the angle.

It is particularly with regard to a space-saving arrangement of the housing shafts and the actuation rollers which are connected to these, in the instrument housing, that a design with which the housing shafts are set obliquely in a direction pointing away from the instrument shank is advantageous. This is particularly the case if, as is preferably envisaged, the housing shafts are arranged in pairs one after the other in the direction of the longitudinal axis of the instrument shank, at two sides of the instrument shank which are away from one another, and if the ends of the housing shafts, at which ends these are drive-connectable to the drive shafts, form the corner points of a rectangle, wherein the shank of the shank instrument is arranged in a plane which is parallel to the rectangle. In this case, the housing shafts are preferably set obliquely in a manner such that they run in the direction normal to the longitudinal extension of the instrument shank obliquely outwards of the surface which is spanned by the ends of the housing shafts. A particularly favorable design, with which the instrument housing tapers into a tip in a plane normal to the longitudinal extension of the instrument shank, can be realized by way of this in a particularly favorable manner. Moreover, hereby sufficient frees space is made available despite a design which is compact per se, by way of a linear guide aligned parallel to the longitudinal extension of the instrument shank being able to be advantageously arranged, and a trocar being able to be coupled onto the shank instrument in a distal manner on the rail of this linear guide.

The housing shafts, alternatively to the described oblique setting or positioning of these, according to a further advantageous design of the drive arrangement according to the invention can also in each case be aligned in a slanted manner in each case in a plane which is aligned parallel to the longitudinal extension of the instrument shank and in which the drive shafts lie. This slanted setting of the housing shafts is useful for example if the shank instrument is to be arranged on a robot arm such that the angle which is enclosed by the shank of the instrument and a middle axis of the robot arm differs from 90°. This design in the case of a suitable angular design permits an arrangement of the shank instrument on a robot arm, with which the instrument shank can be introduced into the body of a patient at a comparatively shallow angle to the body surface of a patient.

Basically, the type of drive connection of the housing shafts to the drive shafts is arbitrary. A particularly compact total unit of the instrument housing and drive unit can then however be realized if, as is preferably envisaged, the housing shafts are coupled in movement to the drive shafts in each case via at least one universal joint or other angle-compensating joints, such as e.g. pod joints. Moreover, the use of these joint types entails a comparatively high efficiency with the transmission of movement from the drive shaft onto the housing shaft.

Typically, one envisages the drive connection of the housing shafts to the drive shafts being created and separated again in a simple and rapid manner. The term universal joint is hereinafter used to represent angle-compensating joint shafts. In this context, it has been found to be useful if the universal joint comprises a first part connected to the housing shaft, and a second part connected to the drive shaft, wherein the first and the second part of the universal joint are connectable to one another via a plug-in connection, which is to say insert connection. The instrument housing which is otherwise designed in a closed manner, comprises openings, via which the parts of the universal joint which are connected to the housing shafts are accessible from the outside, in order to permit the plug-in connection of the first part of the universal joint with its second part. Hereby, an opening formed on the instrument housing is preferably assigned to each housing shaft.

The drive unit advantageously also comprises an essentially closed drive housing. All drive shafts and the drive motors which are assigned to these are arranged in the drive housing. The drive motors are preferably aligned parallel to one another for the compact design of the drive housing. Each drive shaft is preferably aligned in an axially flush manner to the respective associated drive motor. Openings, via which the parts of the universal joint which are connected to the drive shafts are accessible, are formed on the drive housing. The drive housing is preferably connectable to the instrument housing by way of a plug-in connection. Accordingly, plug-in elements which engage with one another on joining together the instrument housing and drive housing are formed on the joining surfaces of the instrument housing and drive housing, said joining surfaces coming to bear on one another and on which the openings for the respective parts of the universal joint are also formed. The drive housing is advantageously dimensioned in a manner such that the drive-housing-side joining surface corresponds to the joining surface formed on the instrument housing, so that the two joining surfaces assume as positive connection.

According to a further advantageous development of the invention, spring elements are provided in the instrument housing, with which spring elements the housing shafts mounted in the instrument housing can be fixed in a defined rotation position, given an instrument housing separated from the drive housing, so as to ensure that a drive connection of the housing shafts arranged in the instrument housing, to the drive shafts arranged in the drive housing, takes place when joining together the instrument housing and the drive housing. The aim of this measure is to position the part of each universal joint which is arranged on the housing shafts such that this part can be connected immediately to the part of the universal joint which is arranged on the drive shafts, by way of sticking together. Hereby, one is typically to also ensure that the parts of the universal joints which are connected to the drive shafts are located in a suitable position. However here too, it is also possible to move these parts of the universal joints into such a position by way of a suitable activation of the drive motors.

Advantageously, a leaf spring which in a locking position engages in each case into a recess which is formed in the region of the outer side of the first part of the universal joint, said first part being arranged on the respective housing shaft, is assigned in the instrument housing to each of the housing shafts which are arranged there, for fastening the housing shafts when the instrument housing is separated from the drive housing. The leaf spring elements are usefully arranged such that they are biased by the drive housing and are thus not engaged, given an instrument housing connected to the drive housing. After separation of the drive housing from the instrument housing, the housing shafts can be manually rotated such that the position of the recess formed on the parts of the universal joint corresponds to the position of the assigned leaf spring element, so that the leaf spring element engages into the recess amid relaxation of the spring. Alternatively to this, it is also possible, before the separation of the drive housing from the instrument housing, by way of a suitable activation of the drive motors then coupled in movement to the housing shafts, to move the housing shafts into a position, in which the position of the recess formed on the parts of the universal joint corresponds to the position of the associated leaf spring element.

Projections which project in the joining direction of the instrument housing and the drive housing and which press the leaf spring elements provided in the instrument housing into an unlocking position on joining the instrument housing and drive housing are advantageously formed on the drive housing, in order to release the locking of the housing shafts which is created by way of the engagement of the leaf spring elements into the recesses formed on the first parts of the universal joints of the housing shafts. Accordingly, the unlocking of the housing shafts is effected solely by way of joining together the instrument housing and the drive housing.

Apart from the possibility, by way of fixing the housing shafts, of ensuring that the first parts of the universal joints which are arranged on the housing shafts are located in a position, in which they can be joined together with the second parts of the universal joint which are arranged on the drive shafts, this can just as well be advantageously ensured by way of the drive shafts being mounted in the drive housing in the axial direction on spring elements and being axially displaceable against spring force in the joining direction of the instrument housing and the drive housing. Alternatively to this, the resilient arrangement can be reversed, so that the housing shafts are mounted in the instrument housing in the axial direction on spring elements and are axially displaceable in the joining direction of the instrument housing and the drive housing against spring force. If with these two designs, the instrument housing and the drive housing are joined together, the second parts of the universal joints which are arranged on the drive shafts contact the first parts of the universal joints which are arranged on the housing shafts, wherein the drive shafts are pushed way from the second parts of the universal joints which are arranged on the housing shafts, in the joining direction of the instrument housing and drive housing, or alternatively the housing shafts are pushed away from the second parts of the universal joints which are arranged on the drive shafts, in the joining direction of the instrument and drive unit, without the first and the second parts of the universal joints forming a plug-in connection. The spring elements, on which the drive shafts, or alternatively the housing shafts are mounted, are biased by way of this. By way of starting the drive motors which are coupled in movement to the drive shafts, the drive shafts with respect to the housing shafts are rotated until the second parts of the universal joints which are arranged on the drive shafts are situated in a position, in which the parts of the universal joint which are arranged on the housing shafts can engage into the second parts of the universal joints which are arranged on the drive shafts, due to a return movement of the drive shafts, or alternatively of the housing shafts, caused by the relaxation of the spring elements.

Usefully, it is to be ensured that the instrument housing and the drive housing can only be joined to one another in a defined position. For this, guide means for the positional fixation of the drive housing on the instrument housing are preferably formed on the joining surfaces of the instrument housing and drive housing. At least two projections projecting in the joining direction and engaging into recesses formed on the other housing can be formed on instrument housing or drive housing, and this is simple with regard to design The projections can advantageously also serve as guide means with a design with which the housing shafts can be fixed by way of leaf spring elements, and projections projecting in the joining direction of the instrument housing and drive housing are formed for releasing the fixation of the housing shafts on the drive housing.

A repeatedly releasable and position-stable connection of the drive housing and the instrument housing, with the drive arrangement according to the invention is preferably realized by way of a fitting bore running through the instrument housing in the joining direction of the instrument housing and drive housing being formed on the instrument housing, and a corresponding fitting bore being formed on the drive housing, in a manner departing from a joining surface to the instrument housing, wherein the fitting bores formed on the drive housing and the instrument housing are provided for receiving a closure pin. Hereby, the closure pin in its position engaging into the fitting bore formed on the drive housing can be fastened on the drive housing and form a fixed constituent of the instrument housing.

Usefully, a second fitting bore which crosses the fitting bore running in the joining direction of the instrument housing and drive housing there is formed on the drive housing, wherein a locking pin which in a locking position engages into a recess formed on the closure pin is displaceably guided in this second fitting bore. The instrument housing and the drive housing are fixedly connected to one another by way of this, wherein an actuation head which is formed at the end of the locking pin and which protrudes at the outer side of the drive housing and is thus easily accessible permits a simple release of the connection of the instrument housing and drive housing.

The invention is hereinafter explained in more detail by way of embodiment examples represented in the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings, in each case in a schematically simplified manner and to different scales:

FIG. 6 is a perspective view of an arrangement of drive motors of the drive unit with drive-side universal shaft joint components for the endoscopic shank instrument according to FIG. 1;

FIG. 14 is a perspective view of a drive shaft which is mounted in a drive housing of the drive unit according to FIG. 1;

FIG. 15 is a perspective sectional view according to FIG. 14;

FIG. 18 is a perspective sectional view according to FIG. 16;

FIG. 19 is a perspective sectional view according to FIG. 17;

FIG. 20 is a perspective view of a drive arrangement for an endoscopic shank instrument which is arranged on a robot arm, in a second embodiment;

FIG. 21 is a perspective view of a drive arrangement in a further embodiment;

FIG. 22 is a perspective view of an endoscopic shank instrument which is arranged on a robot arm of an operation robot and which is according to a further embodiment;

FIG. 23 is a perspective view of an endoscopic shank instrument which is arranged on a second robot arm of an operation robot.

DESCRIPTION OF THE PREFERRED EMBODIMENTS

Figure 1:
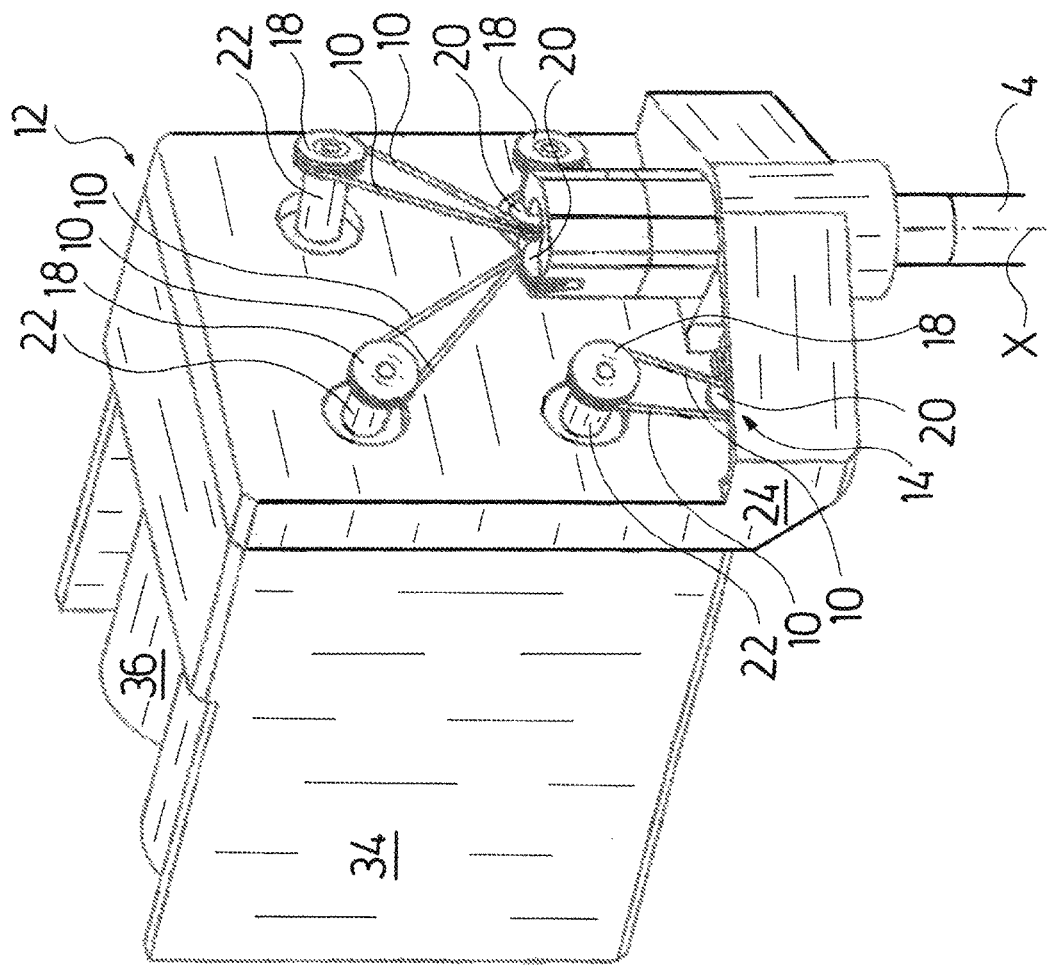
FIG. 1 is a perspective view of a proximal end section of an endoscopic shank instrument with a connected drive housing and drive motors, without a housing part of the instrument.
Figure 2:
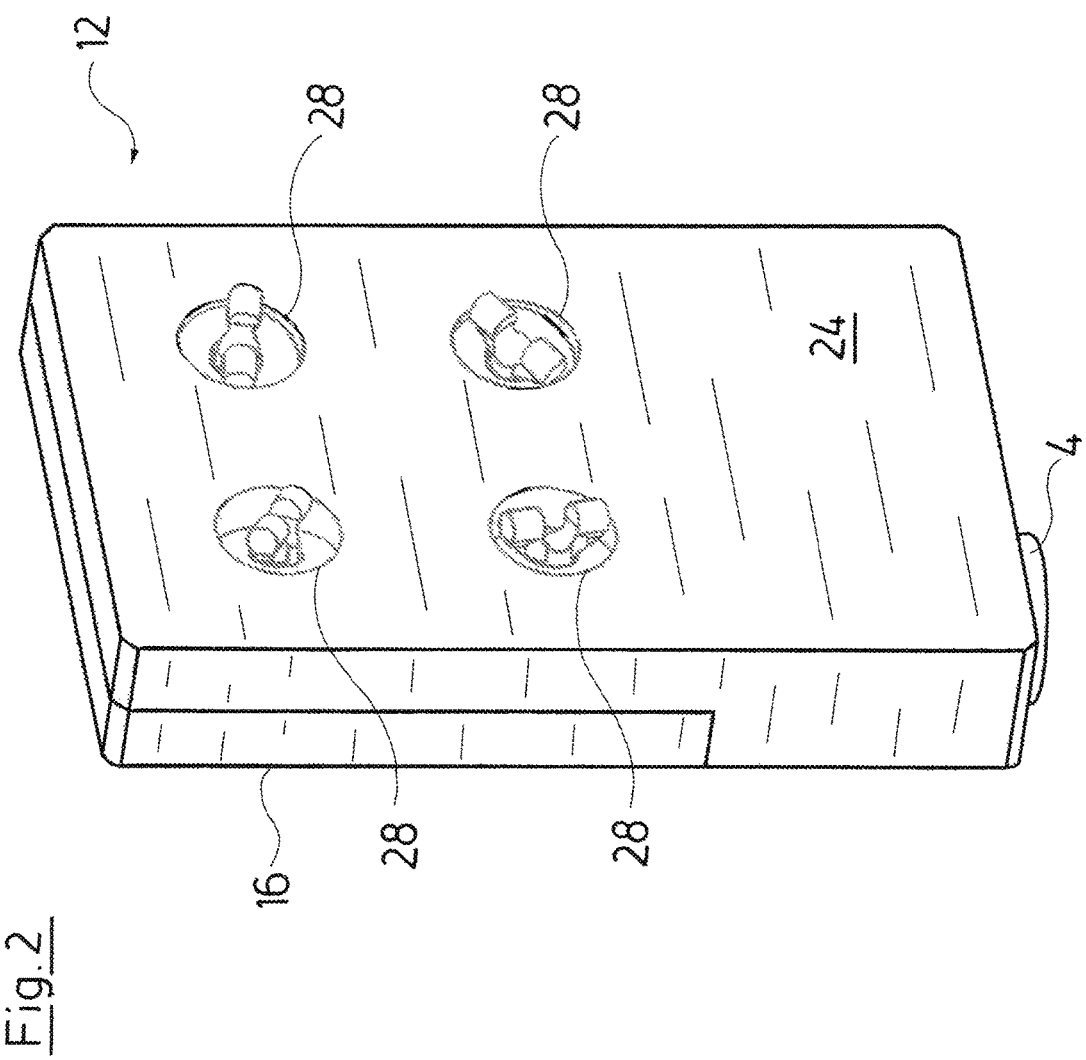
FIG. 2 is a perspective view of a proximal end section of the endoscopic instrument according to FIG. 1, without a representation of any locking mechanisms between the drive unit and instrument.
Figure 3:
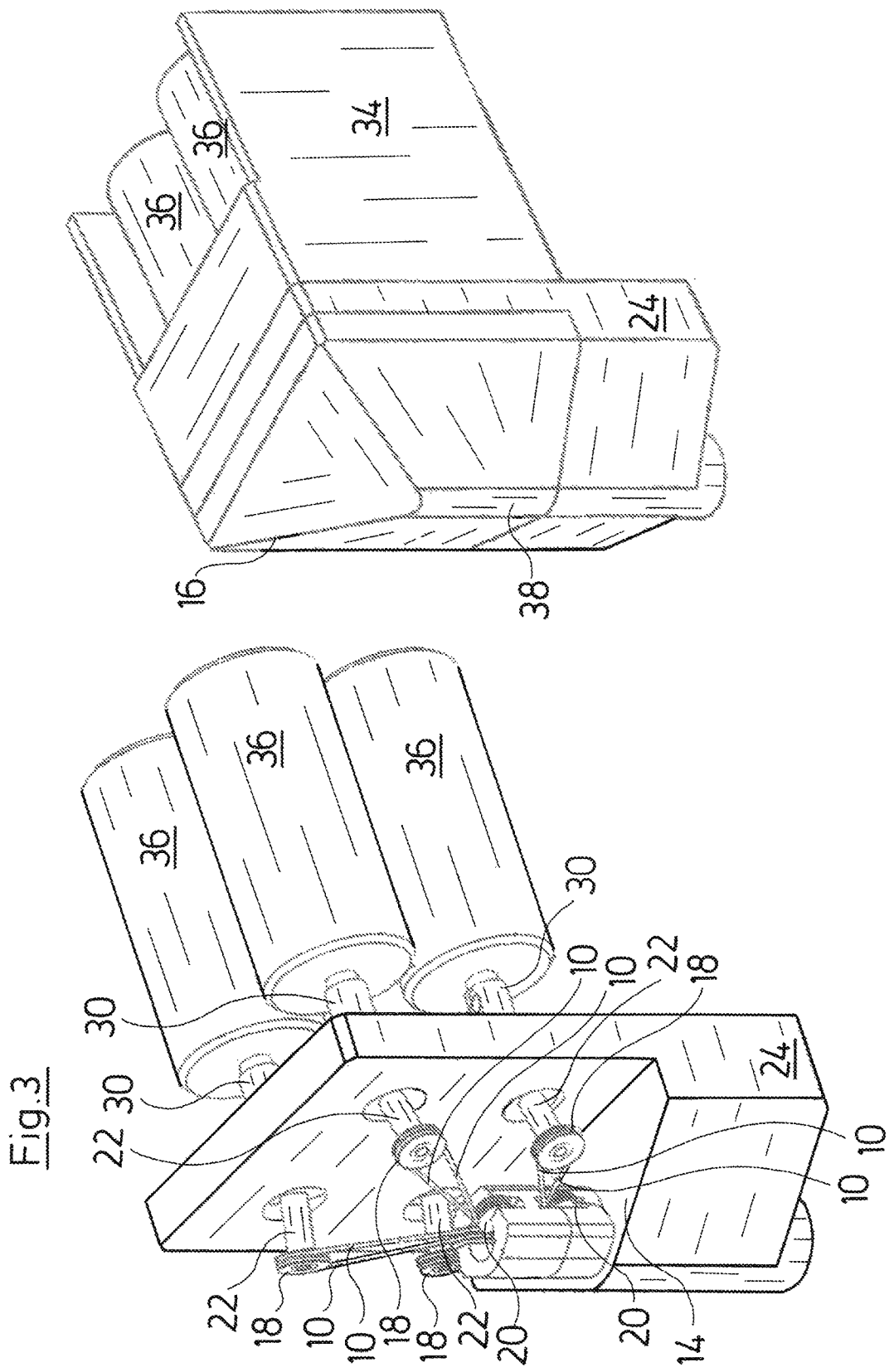
FIG. 3 is perspective view of a drive arrangement for the endoscopic shank instrument according to FIG. 1, without a housing part of the instrument as well as without the drive housing.
Figure 4:
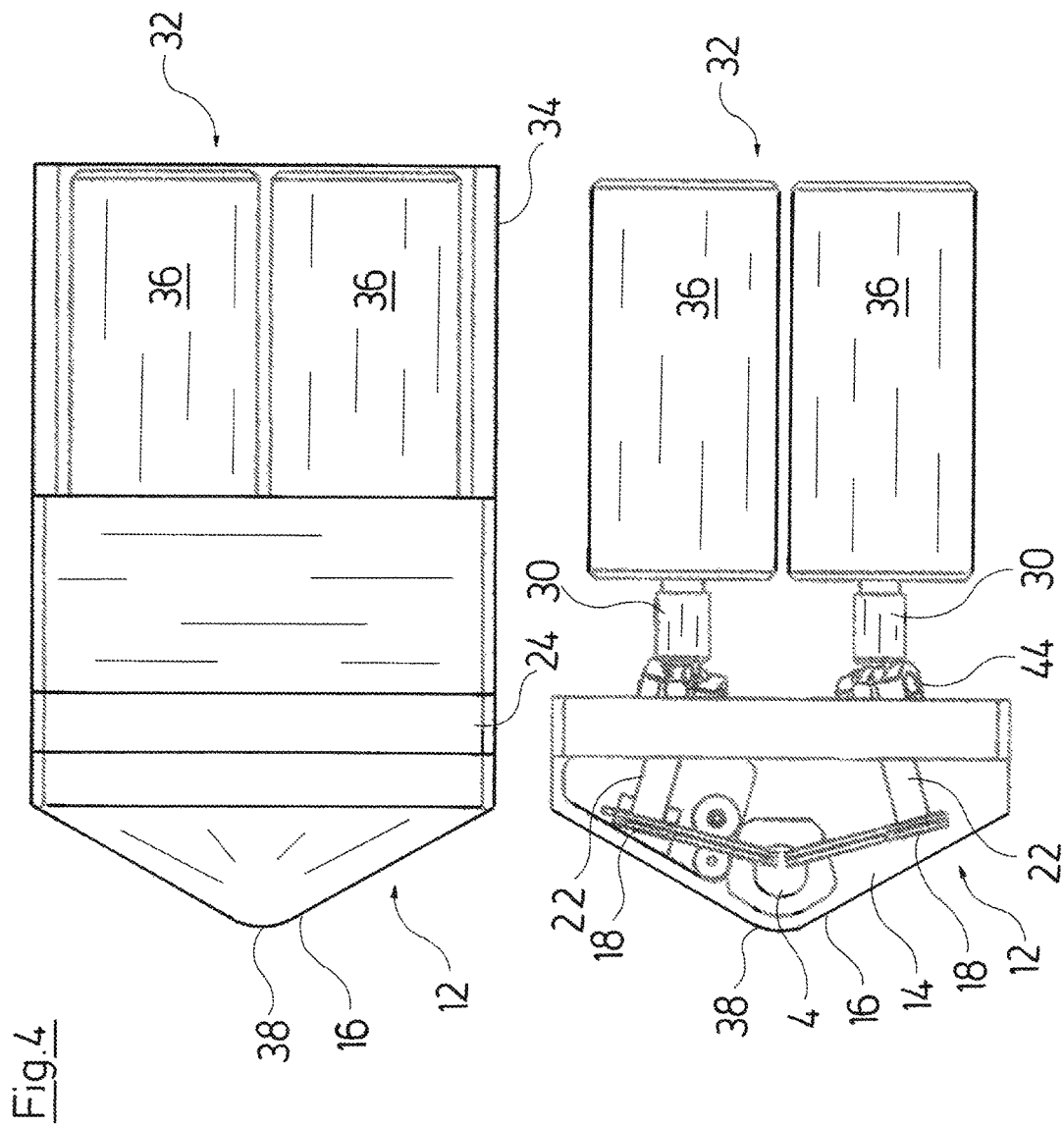
FIG. 4 is a plan view of the drive arrangement according to FIG. 3.
Figure 5:
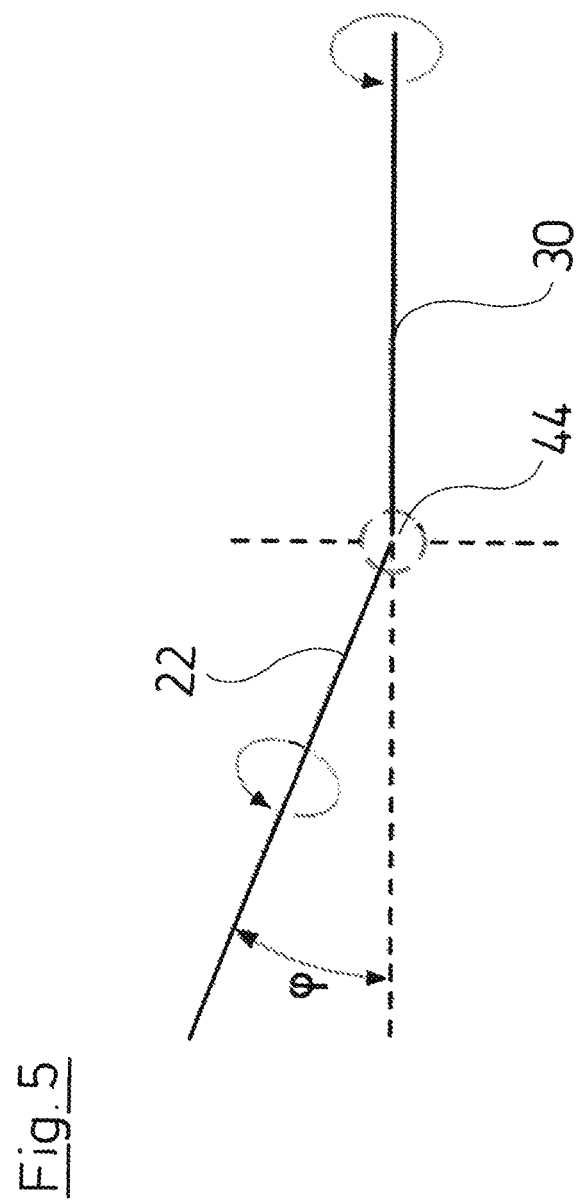
FIG. 5 is a geometric basic sketch of a drive train of the drive arrangement according to FIG. 3.

The endoscopic shank instrument which is represented in the FIGS. 1 and 2 is provided for the arrangement on a robot arm 2 of a surgical operation robot (FIGS. 20, 22 and 23). It comprises an elongate, rigid instrument shank 4. The instrument shank in FIGS. 1 and 2 has been almost completely omitted for purposes of a better overview, but it corresponds to the instrument shank 4 of the endoscopic shank instrument which is represented in FIGS. 21 to 23. With regard to the instrument shank 4 it is the case of a hollow shank. As with the shank instrument represented in FIGS. 21 to 23, an instrument head 6 with angular bending kinematics 7 and with a tool 8 is also arranged on the distal shank end of the shank instrument which is represented in FIGS. 1 and 2. The tool 8 can be angled relative to the instrument shank 4 by way of the angular bending kinematics 7.

Pull means or pull device in the form of six pull cables 10 which are led through the instrument shank 4 into an instrument housing 12 arranged at the proximal shank end are provided for the control of the angling of the tool 8, which in the present case it is the case of a jaw tool. Two further pull means in the form of pull cables 10 which are arranged in the instrument housing 12 are provided for the control of the rotation of the instrument shank 4 about its longitudinal axis X.

The pull cables 10 are fastened in a paired manner on four actuation rollers 18, in a free space 14 which is formed in the instrument housing 12 and which is covered by a housing part 16 of the instrument housing 12, wherein beforehand these pull cables are deflected at deflection rollers 20 rotatably mounted in the free space 14, from the instrument shank 4 in the direction of the actuation rollers 18. The actuation rollers 18 are fastened on the ends of housing shafts 22 which are led through a plate-like section of a main body 24 of the instrument housing 12 and are rotatably mounted in this section of the main body 24 in bearing bushings (FIGS. 14 to 19), wherein the plate-like section is aligned parallel to the longitudinal axis X of the instrument shank 4. The housing shafts 22 are arranged on the main body 24, in a paired manner in the direction of the longitudinal axis X of the instrument shank 4, on two sides of the instrument shank 4 which are away from one another.

The housing shafts 22 are led completely through the main body 24, so that the ends of the housing shafts 22 which are away from the actuation rollers 18 protrude at the rear side of the main body 24 which is away from the free space 14. The ends of the housing shafts 22 which project or protrude at the rear side of the main body 24 are designed in a fork-like manner and are arranged in the region of cylindrical deepenings (recesses) which are formed on the main body, wherein this will be detail with in more detail hereinafter.

The housing shafts 22 with the drive shafts 30 of a drive unit 32 are drive connectable in a repeatedly releasably manner, at the ends projecting at the rear side of the main body 24. Each of the four drive shafts 30 are coupled in movement to the motor shaft of a drive motor 36, via gear means which are not represented in the drawing, in a drive housing 34 of the drive unit 32.

All four drive shafts 30 are aligned normally to the longitudinal axis X of the instrument shank 4 in the drive-connected condition. The housing shafts 22 with all embodiments of the drive arrangement for an endoscopic shank instrument which are represented in the drawings are aligned obliquely to the drive shafts 30.

With the designs represented in the FIGS. 1 to 5 as well as 20, the housing shafts 22 are set obliquely in a manner pointing away from the instrument shank 4. It is particularly this alignment of the housing shafts 22 and the alignment of the actuation rollers 18 entailed by this which permits the free space 14 to taper into a tip at an angle of 120°, in a plane perpendicular to the longitudinal axis X of the instrument shank 4. In a manner corresponding to this, the housing part 16, in an end section which is away from the main body 26 also tapers into a ridge 38 running parallel to the longitudinal axis X of the instrument shank 4. The instrument shank 4 runs out into the free space 14 of the instrument housing 12, in the direct proximity of this ridge 38.

Figure 24:
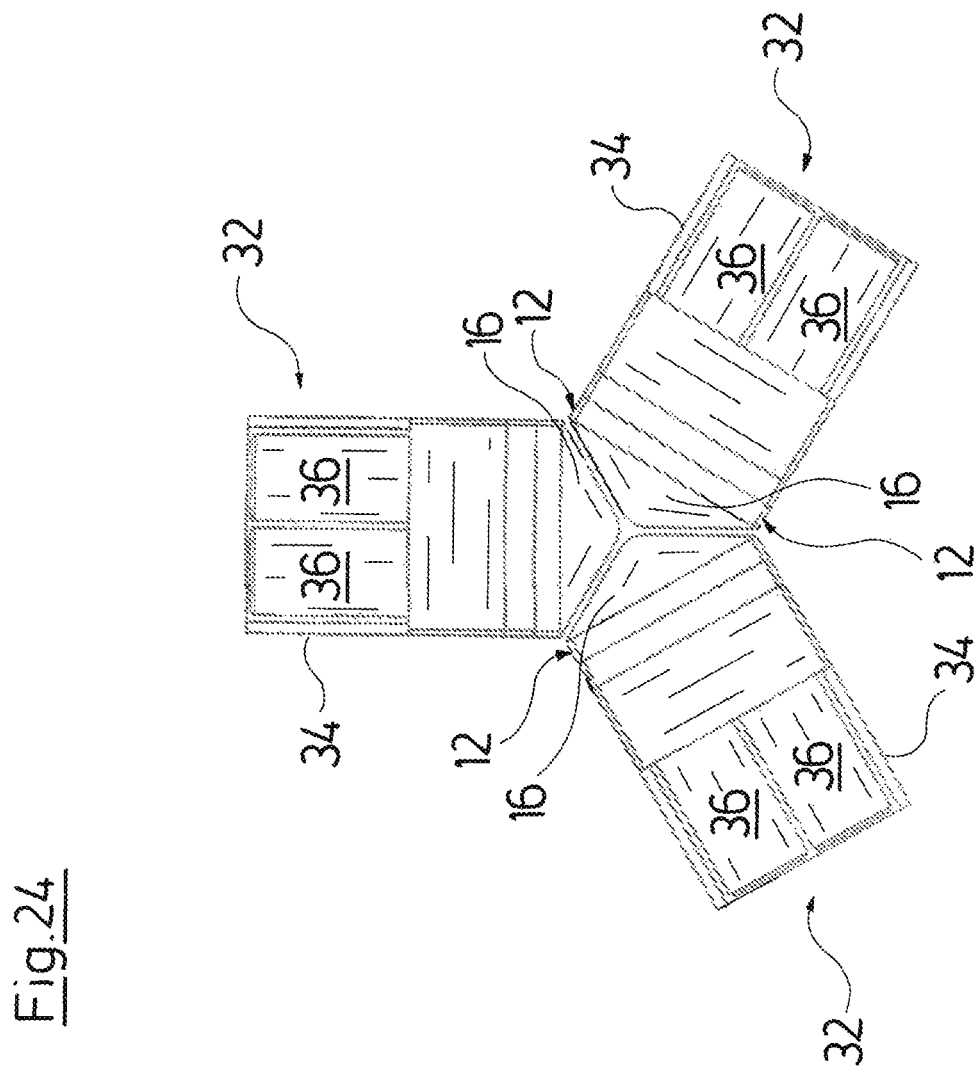
FIG. 24 is a plan view of a basic representation of three endoscopic shank instruments with a drive arrangement according to FIG. 3, with a single port operation.

The advantages of the design of the instrument housing 12 or its housing part 16 and of the oblique alignment of the housing shafts 22 are clear from FIGS. 20 and 24. As FIG. 24 represents, the tapering of the instrument housing 12 at an angle of 120° into a ridge 38 allows three shank instruments to be simultaneously used with a single-port operation, since the instrument shanks 4 can be located in the direct proximity to one another and can thus be introduced commonly via a single body opening, into the body of a patient. It is evident from FIG. 2 that, on account of the arrangement and the alignment of the housing shafts 22 with the actuation rollers 18 which are arranged thereon and are between the housing shafts 22 arranged in pairs in the direction of the longitudinal axis X of the instrument shank 4, there is sufficient space in the instrument housing 12 for a linear guide which is aligned parallel to the longitudinal axis X of the instrument shank 4 and on whose rail 40 a trocar 42 can be led on the distal end, wherein the instrument section 4 is guided by the trocar 42 (FIGS. 22 and 23).

Apart from a design, with which the housing shafts 22 are set obliquely in a direction pointing away from the instrument shank 4, there is also the possibility of aligning the housing shafts 22 in a slanted manner parallel to the plane which is aligned parallel to the longitudinal extension of the instrument shank 4 and in which the drive shafts 30 or their longitudinal axes Y lie. This alignment of the housing shafts 22 creates the possibility of arranging the instrument shank 4 on the instrument housing 12 in a manner such that an angle which is enclosed by the instrument shank 4 and a middle axis of a distal end section of the robot arm 2 or the longitudinal axes Y of the drive shafts 30 differs from an angle of 90°, as is represented in FIGS. 21, 22 and 23.

Figure 17:
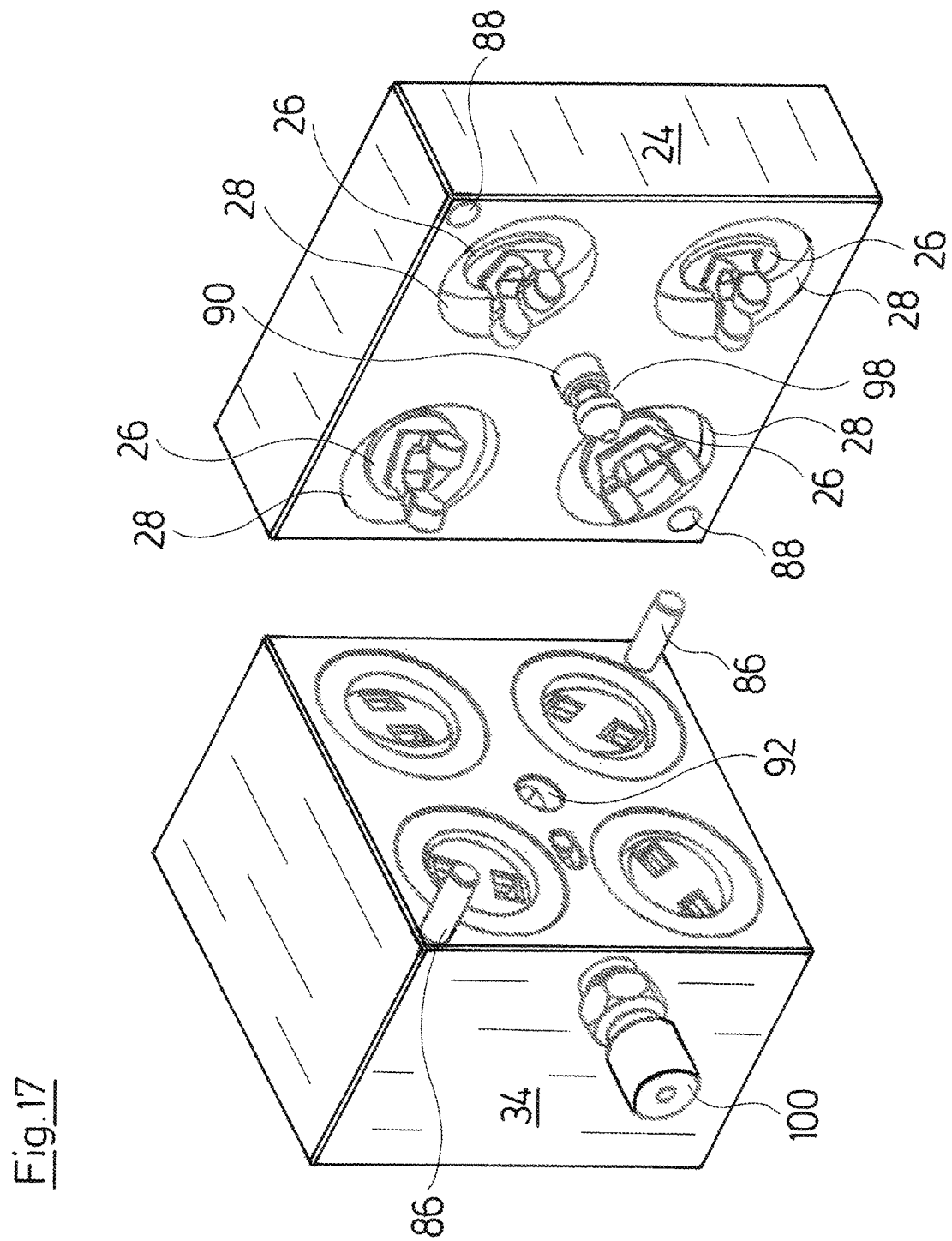
FIG. 17 is a perspective view according to FIG. 16, with a drive housing separated from the instrument housing.

The arrangement which is represented in FIG. 22 and FIG. 23 describes the fastening sequence of the robot arm 2, instrument housing 12 and drive unit 32. The instrument housing 12 is again repeatedly releasably coupled at a first region onto the robot arm and at a second region onto a drive unit 32. The drive unit 32 is hereby supported exclusively on the main body 24 as well as the universal joint 44, 44' and the closure mechanism (FIG. 17 to FIG. 19).

Figure 7:
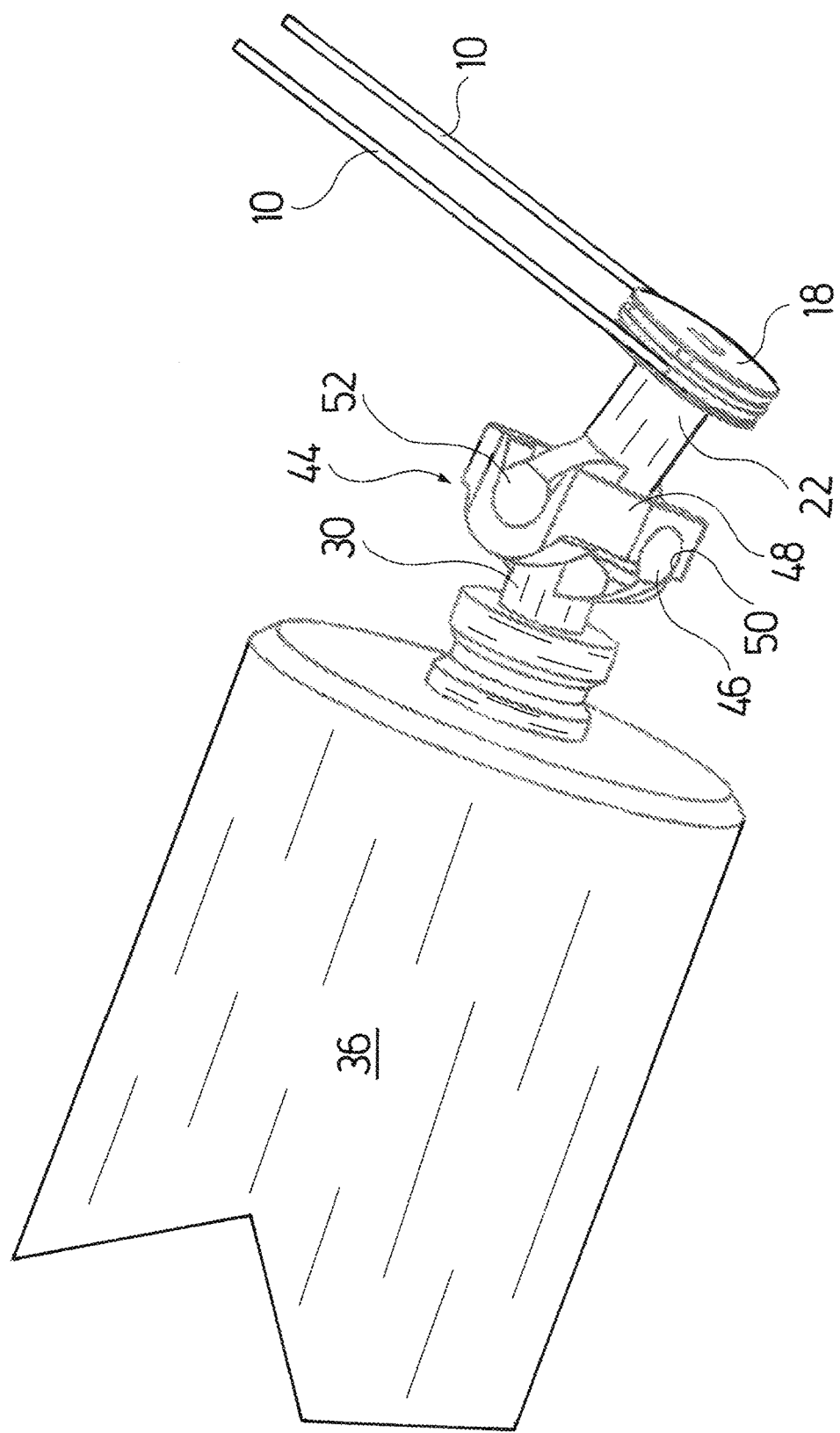
FIG. 7 is a perspective view of a universal shaft joint of the drive shaft arrangement according to FIG. 3, omitting the shaft mounting.

The housing shafts 22 which are arranged in the instrument housing 12 are drive-connectable to the drive shafts 30 of the drive unit 32 via a universal joint 44 and 44'. One possible design of a universal joint 44 is represented in FIG. 7. Here, the end of the drive shaft 30 which is away from the drive motor 36 divides in a fork-like manner into two end sections, wherein roller bodies 46 are arranged at the ends of the end sections, and the common middle axis of these roller bodies is aligned normally to the longitudinal axis Y of the drive shaft 30. A wobble element 48 is arranged on the drive shaft 30. The wobble element 48 is designed in an essentially annular manner, wherein two recesses 50 which correspond to the shape of the roller bodies 46 and into which the roller bodies 46 engage are formed on a face side on the wobble element 48, in a manner lying opposite one another. The wobble element 48 is positively connected to the drive shaft 30 by an undercut formed on the two recesses 50, wherein this wobble element is pivotable about a pivot axis which is formed by the middle axes of the roller bodies 46. As has already been noted, the ends of the housing shafts 22 which are provided for the drive connection to the drive shafts 30 likewise divide into two end-sections in a fork-like manner, wherein roller bodies 52 whose common middle axis is aligned normally to the longitudinal axis Y of the housing shaft 22 are formed on the ends of the end-sections. Two recesses 54 are formed on the wobble element 48 on a face side which is away from the recesses 50, in a manner offset to the recesses 50 by 90°, for receiving the roller bodies 52 which are arranged on the end section of the housing shaft 22. These recesses 54 in an inner end region have a shape corresponding to the roller bodies 52, wherein the recesses 54 however widen in the direction of their face-side opening.

Figure 8:
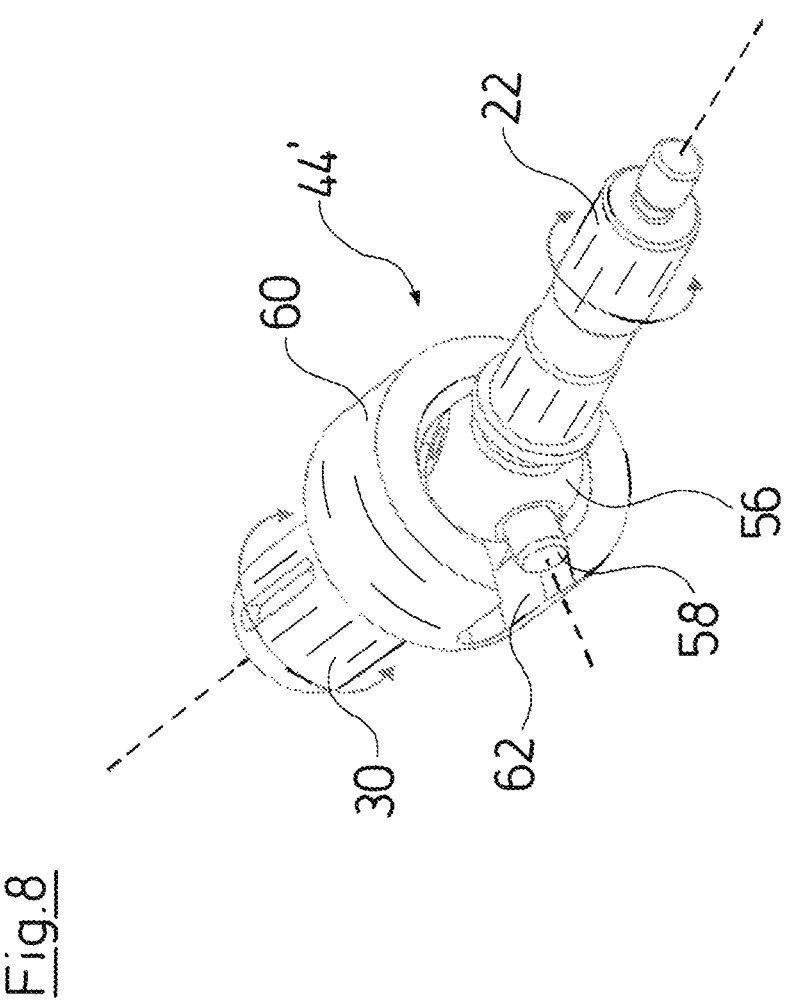
FIG. 8 is a perspective view of a universal shaft joint of the drive arrangement according to FIG. 3, according to a second embodiment.
Figure 9:
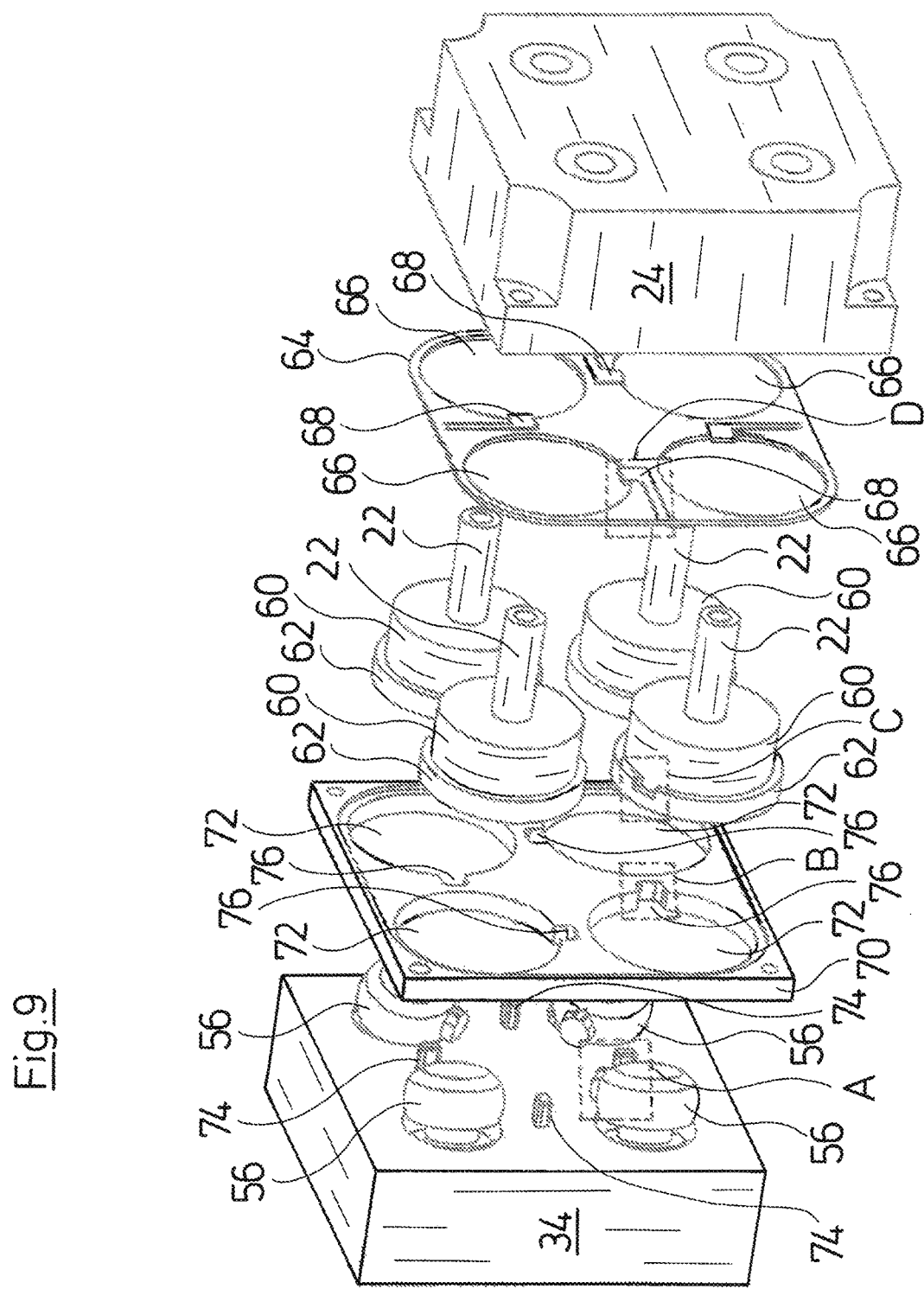
FIG. 9 is a perspective view of a variant of the connection location between the instrument and drive unit of the drive arrangement according to FIG. 3, in a perspective exploded representation, in a reduced form.
Figure 11:
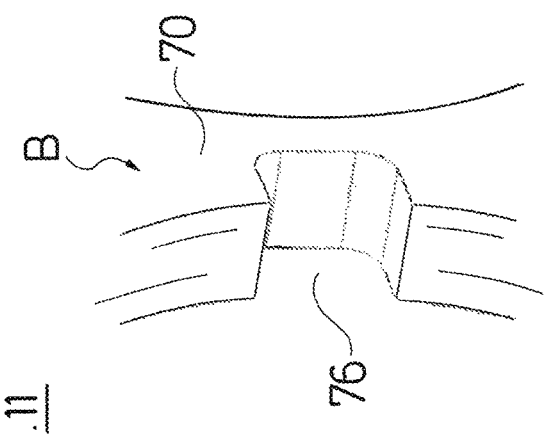
FIG. 11 is a detail view of a detail B of FIG. 9.
Figure 13:
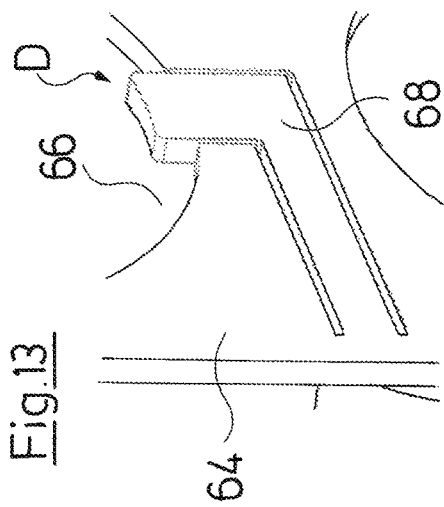
FIG. 13 is a detail view of a detail D of FIG. 9.
Figure 10:
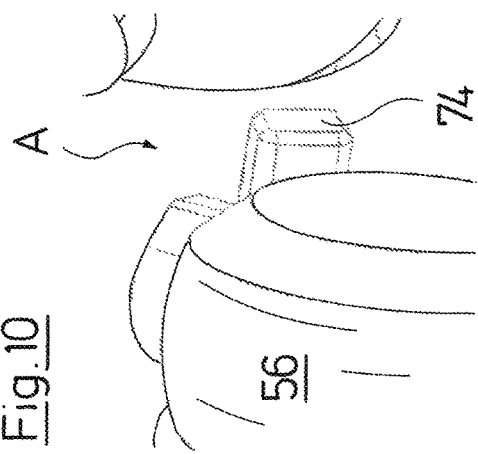
FIG. 10 is a detail view of detail A of FIG. 9.
Figure 12:
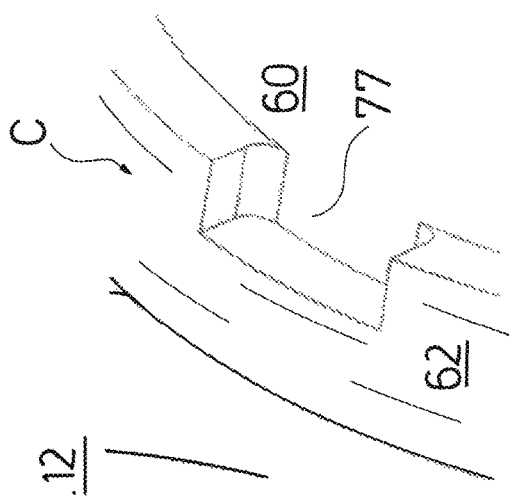
FIG. 12 is a detail view of a detail C of FIG. 9.
Figure 16:
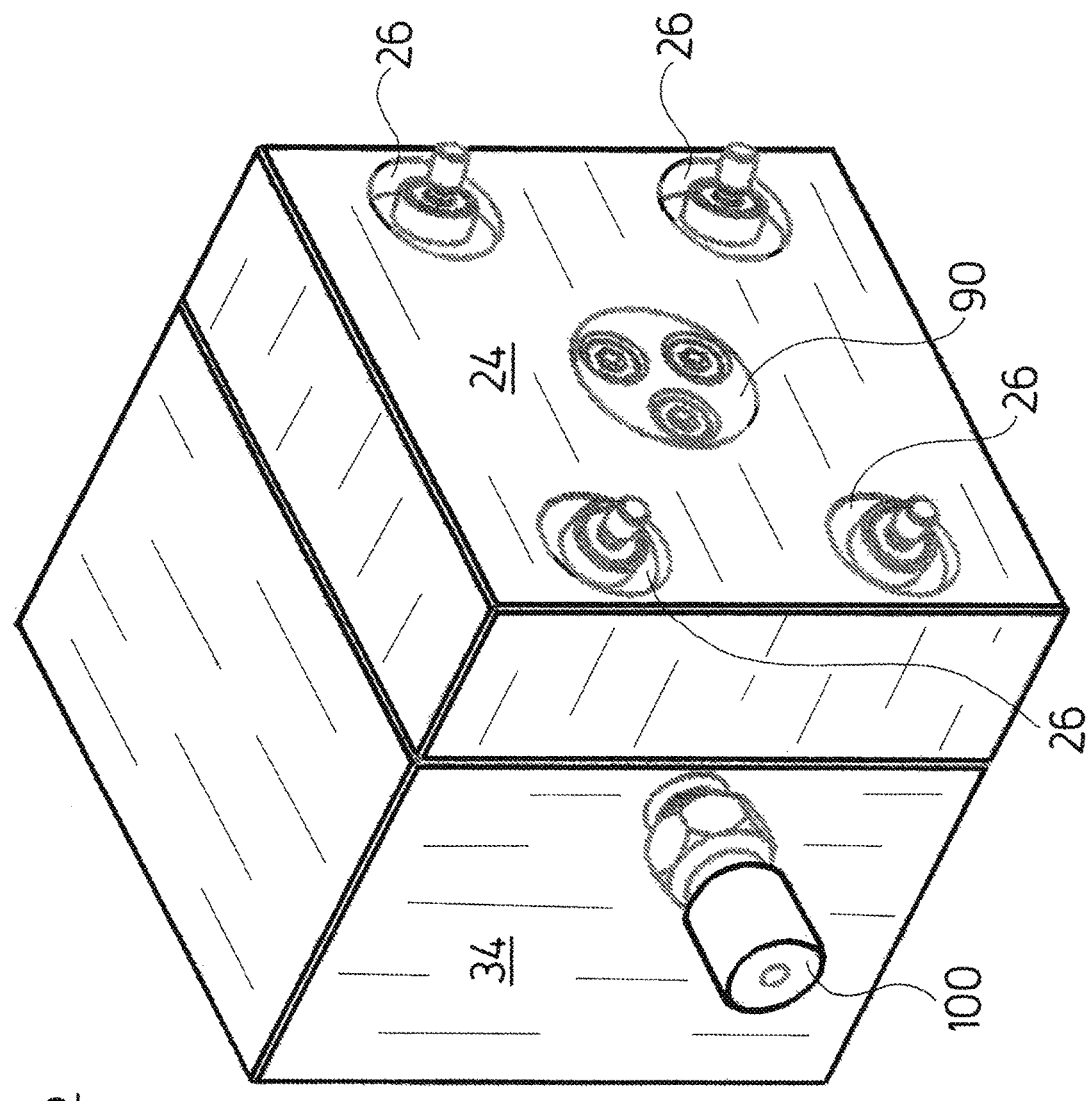
FIG. 16 is a perspective view of a basic representation of the drive arrangement according to FIG. 3, omitting the actuation rollers, the instrument shank as well as the instrument head and detailed housing designs.

A further embodiment example of a universal joint 44' which can be applied with the drive arrangement according to the invention is represented in FIG. 8. Here, a ball head 56, on which a cylindrical pin 58 projects transversely to the longitudinal extension of the housing shaft 22 is formed on the end of the housing shaft 22, said end projecting at the side of the main body 24 which is away from the free space 14. A bushing 60 which is open in the longitudinal direction of the drive shaft 30 is arranged at the free end of the drive shaft 30. The ball head 56 arranged on the housing shaft 22 engages into this bushing 60, wherein the pin 58 arranged on the ball head 56 is guided in a guide groove 62 which is formed on the bushing 60 and which departing from the open end of the bushing 60 extends in the longitudinal direction of the drive shaft 30.

A design, with which housing shafts 22 mounted in the instrument housing 12 can be fixed in a fixed rotation position by way of spring elements given an instrument housing 12 separated from the drive housing 34, can be deduced from the FIGS. 9 to 13. Here, bushings 60 which form part of the universal joint 40' are arranged on the ends of the housing shafts 22 which are away from the actuation rollers 18. An annular collar 62 which projects in the radial direction is formed on the end of the bushings 60 which is at the outside in the longitudinal direction of the housing shafts 22.

A spring segment plate 64 is arranged on the outer side of the main body 24 of the instrument housing 12, said outer side being away from the free space 14. The spring segment plate 64 comprises four circular recesses 66, whose position and size corresponds to the recesses 28 formed on the main body 24. Four L-shaped leaf spring elements 68 are cut out on the spring segment plate, and the end section of these leaf spring elements 68 projects in each case into one of the recesses 66. The spring segment plate 64 is held on the main body 24 of the instrument housing 12 by way of a cover plate 70 which at the outer side of the spring segment plate 64 is fastened on the main body 24. As is the case with the spring segment plate 64, the cover plate 70 also comprises four circular recesses 72 whose position and size corresponds to the recesses 28 formed on the main body 24.

The bushings 60 which are formed on the housing shafts 22 engage into the recesses 28 formed on the main body 24. Hereby, the leaf spring elements 68 come to bear on the collar 62 formed on the bushings 60 and are biased by way of this. The housing shafts 22 however can be manually rotated such that the position of a recess 72 formed on the collar 62 corresponds to the position of the end of the leaf spring element 68 which projects into the recess 66 of the spring segment plate 64, so that the leaf spring element 68 relaxes and engages into the recess 72. The housing shafts 22 are secured from rotating or twisting by way of this, and are held in a fixed position.

Ball heads 56 which likewise form a part of the universal joint 44' are formed on the ends of the drive shafts 30 which project out of the drive housing 34. The ball heads 56 engage into the bushings 60 which are formed on the housing shafts 22, on joining together the instrument housing 12 and the drive housing 34. Pins 74 projecting on the drive housing 34 in the axial direction of the drive shafts 30 simultaneously engage through recesses 76 which are formed on the outer edge of the recesses 72 of the cover plate 70 and in each case expose a region of the leaf spring elements 68. The leaf spring elements 68 are pressed out of the recess 77 formed on the collar 62 by way of this, so that the housing shafts 22 are freely rotatably again.

FIGS. 14 and 15 show a design, with which a free shaft end of the drive shaft 30 is formed by a sleeve 78 which is supported on the drive shaft via a spring element in the form of a helical spring 80. A longitudinal groove 82, into which a radially aligned pin 82 arranged on the drive shaft 30 engages, is formed on the sleeve 78, in order to prevent a rotation of the sleeve 78 relative to the drive shaft 30. If with this design, the instrument housing 12 and the drive housing 34 are joined together, then the end section of the housing shaft 22 which forms a part of a universal joint 44 contacts a wobble element 48 arranged in the sleeve 78, without the end section of the housing shaft having to engage into recesses formed on the wobble element 48. The sleeve 78 is displaced away from the instrument housing in the axial direction whilst biasing the helical spring 80. By way of starting the drive motor 36 coupled in movement to the drive shaft 30, the drive shaft 30 is rotated with respect to the housing shaft 22, until the end section of the drive shaft 30 is located in a position, in which the end section of the housing shaft 22 and the wobble element 48 can form a plug-in connection, and the sleeve 78 with the wobble element 48 is moved back in the direction of the housing shaft 22 amid relaxation of the helical spring 80.

It can also be deduced from FIGS. 16 to 19, that in a special embodiment, two guide pins 86 are arranged on the joining surface of the drive housing 34, and these guide pins 86 on joining together the instrument housing 12 and drive housing 34 engage into recesses 88 which are formed on the instrument housing 12. Moreover, from these figures, it can be deduced that a closure pin 19 which is led through a fitting bore running in the joining direction of the instrument housing 12 and the drive housing 34 and formed on the main body 24 is fastened on the main body 24 of the instrument housing 12. On joining together the instrument housing 12 and the drive housing 34, an end section of the closure pin 90° which projects at the side of the main body 24, said side being away from the free space 14, engages into a fitting bore 92 formed on the drive housing 34. A further fitting bore 94 which crosses the fitting bore 92 is formed on the drive housing 34. A locking pin 96 with an actuation head 100 arranged outside the drive housing 34 is guided in an axially displaceable manner in the fitting bore 94, and can be displaced into a position, in which it engages into an annular groove 98 formed on the closure pin 90, by which means the connection of the drive housing 34 and the instrument housing 12 is secured.

While specific embodiments of the invention have been shown and described in detail to illustrate the application of the principles of the invention, it will be understood that the invention may be embodied otherwise without departing from such principles.

The invention claimed is:

1. A drive arrangement for an endoscopic shank instrument, the drive arrangement comprising:
   an instrument housing at the proximal shank end;
   at least one housing shaft which is rotatably mounted in the instrument housing and which is repeatedly releasably drive-connected to a pull device, said pull device being provided at a distal shank end for the control of an instrument head;
   a drive unit with at least one drive shaft, the drive shaft being drive-connectable with the at least one housing shaft, wherein the at least one housing shaft is aligned obliquely to the drive shaft drive connected thereto; and
   further housing shafts, wherein four housing shafts are arranged in pairs one after the other in a direction of a longitudinal axis of the instrument shank, at two sides of the instrument shank which are away from one another.

2. A drive arrangement according to claim 1, wherein the drive unit comprises at least another drive shaft to provide at least two drive shafts which are aligned at an angle to one another and drive-connectable to an equal number of housing shafts.

3. A drive arrangement according to claim 1, wherein the drive unit comprises at least another drive shaft to provide the drive unit with at least two drive shafts which are aligned parallel to one another and drive- connectable to an equal number of housing shafts, wherein the axes of the individual drive shaft and housing shaft within each paired assignment are aligned in an oblique manner.

4. A drive arrangement for an endoscopic shank instrument, the drive arrangement comprising:
   an instrument housing at the proximal shank end;
   at least one housing shaft which is rotatably mounted in the instrument housing and which is repeatedly releasably drive-connected to a pull device, said pull device being provided at a distal shank end for the control of an instrument head; and
   a drive unit with at least one drive shaft, the drive shaft being drive-connectable with the at least one housing shaft, wherein the at least one housing shaft is aligned obliquely to the drive shaft drive connected thereto, the drive unit having an essentially closed drive housing which is connectable to the instrument housing by way of a plug-in connection, wherein the at least one drive shaft in the drive housing is mounted in the axial direction on one or more springs elements and is axially displaceable against spring force, counter to the joining direction of the instrument housing and drive housing.

5. A drive arrangement according to claim 1, wherein the instrument housing tapers, in a plane normal to the longitudinal extension of the instrument shank, into a tip.

6. A drive arrangement according to claim 1, wherein the housing shaft in the instrument housing is set obliquely in a direction pointing away from the instrument shank.

7. A drive arrangement according to claim 1, wherein the housing shaft in the instrument housing is aligned in a slanted manner in a plane which is aligned parallel to the longitudinal extension of the instrument shank and in which the at least one drive shaft lies.

8. A drive arrangement according to claim 1, wherein the drive unit has an essentially closed drive housing which is connectable to the instrument housing by way of a plug-in connection.

9. A drive arrangement according to claim 8, further comprising spring elements provided in the instrument housing, the at least one housing shaft being mounted in a fixed rotational position via at least one of the spring elements with the instrument housing separated from the drive housing.

10. A drive arrangement according to claim 8, wherein the at least one housing shaft in the instrument housing is mounted in an axial direction on one or more spring elements and is axially displaceable against spring force, counter to the joining direction of the instrument housing and the drive housing.

11. A drive arrangement according to claim 8, wherein the at least one drive shaft in the drive housing is mounted in the axial direction on one or more springs elements and is axially displaceable against spring force, counter to the joining direction of the instrument housing and drive housing.

12. A drive arrangement according to claim 8, wherein a guide means for the positional fixation of the drive housing on the instrument housing is provided on the joining surfaces of the instrument housing and drive housing.

13. A drive arrangement for an endoscopic shank instrument, the drive arrangement comprising:
an instrument housing at the proximal shank end;
at least one housing shaft which is rotatably mounted in the instrument housing and which is repeatedly releasably drive-connected to a pull device, said pull device being provided at a distal shank end for the control of an instrument head; and
a drive unit with at least one drive shaft, the drive shaft being drive-connectable with the at least one housing shaft, wherein the at least one housing shaft is aligned obliquely to the drive shaft drive connected thereto, wherein the housing shaft is coupled in movement to the drive shaft via at least one universal joint.

14. A drive arrangement according to claim 13, wherein the universal joint comprises a first part which is connected to the housing shaft and a second part which is connected to the drive shaft, wherein the first and the second part of the universal joint are connectable to one another by a plug-in connection.

15. A drive arrangement for an endoscopic shank instrument, the drive arrangement comprising:
an instrument housing at the proximal shank end;
at least one housing shaft which is rotatably mounted in the instrument housing and which is repeatedly releasably drive-connected to a pull device, said pull device being provided at a distal shank end for the control of an instrument head;
a drive unit with at least one drive shaft, the drive shaft being drive-connectable with the at least one housing shaft, wherein the at least one housing shaft is aligned obliquely to the drive shaft drive connected thereto, the drive unit having an essentially closed drive housing which is connectable to the instrument housing by way of a plug-in connection;
spring elements provided in the instrument housing, the at least one housing shaft being mounted in a fixed rotational position via at least one of the spring elements with the instrument housing separated from the drive housing, wherein a leaf spring element of the spring elements in the instrument housing is assigned to each housing shaft, said leaf spring element in a locking position in each case engaging into a recess which is formed in the region of an outer side of the first part of the universal joint, said first part being arranged on the respective housing shaft.

16. A drive arrangement according to claim 15, wherein projections which project in a joining direction of the instrument housing and the drive housing are formed on the drive housing and on joining together the instrument housing and the drive housing move the leaf spring elements provided in the instrument housing into an unlocking position.

17. A drive arrangement for an endoscopic shank instrument, the drive arrangement comprising:
an instrument housing at the proximal shank end;
at least one housing shaft which is rotatably mounted in the instrument housing and which is repeatedly releasably drive-connected to a pull device, said pull device being provided at a distal shank end for the control of an instrument head; and
a drive unit with at least one drive shaft, the drive shaft being drive-connectable with the at least one housing shaft, wherein the at least one housing shaft is aligned obliquely to the drive shaft drive connected thereto, the drive unit having an essentially closed drive housing which is connectable to the instrument housing by way of a plug-in connection, wherein a fitting bore running through the instrument housing in the joining direction of the instrument housing and the drive housing is formed on the drive housing, and a corresponding fitting bore is formed on the drive housing in a manner departing from a joining surface to the instrument housing, wherein the fitting bores which are formed on the drive housing and the instrument housing are provided for receiving a closure pin.

18. A drive arrangement according to claim 17, wherein a second fitting bore is formed on the instrument housing and crosses the fitting bore running in the joining direction of the instrument housing and drive housing, in which second fitting bore a locking pin is displaceably guided, said locking pin in a locking position engaging into a recess formed on the closure pin.

19. A drive arrangement for an endoscopic shank instrument, the drive arrangement comprising:
an instrument housing at the proximal shank end;
at least one housing shaft which is rotatably mounted in the instrument housing and which is repeatedly releasably drive-connected to a pull device, said pull device being provided at a distal shank end for the control of an instrument head; and
a drive unit with at least one drive shaft, the drive shaft being drive-connectable with the at least one housing shaft, wherein the at least one housing shaft is aligned obliquely to the drive shaft drive connected thereto, the drive unit having an essentially closed drive housing which is connectable to the instrument housing by way of a plug-in connection, wherein the at least one housing shaft in the instrument housing is mounted in an axial direction on at least one spring element and is axially displaceable against spring force, counter to the joining direction of the instrument housing and the drive housing.

* * * * *